(12) United States Patent
Klintz et al.

(10) Patent No.: US 6,255,489 B1
(45) Date of Patent: Jul. 3, 2001

(54) METHOD FOR PRODUCING (HETERO) AROMATIC HYDROXYLAMINES

(75) Inventors: Ralf Klintz, Grünstadt; Norbert Götz, Worms; Michael Keil, Freinsheim; Manfred Heilig, Ludwigshafen; Horst Wingert, Mannheim; Uwe Josef Vogelbacher, Ludwigshafen; Josef Wahl, Schifferstadt; Frank Wetterich, Mutterstadt; Gregor Daun, Heidelberg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/486,500

(22) PCT Filed: Aug. 21, 1998

(86) PCT No.: PCT/EP98/05332

§ 371 Date: Feb. 29, 2000

§ 102(e) Date: Feb. 29, 2000

(87) PCT Pub. No.: WO99/12911

PCT Pub. Date: Mar. 18, 1999

(30) Foreign Application Priority Data

Sep. 5, 1997 (DE) .............................. 197 38 864
Sep. 5, 1997 (DE) .............................. 197 38 862

(51) Int. Cl.⁷ ..................... C07D 221/00; C07C 249/00
(52) U.S. Cl. ..................... 546/159; 564/256; 564/300; 564/336
(58) Field of Search .................. 546/159; 564/256, 564/300, 336

(56) References Cited

U.S. PATENT DOCUMENTS 3,544,485   12/1970   Taira ...................................... 252/477
4,415,753   11/1983   Caskey ................................... 564/418

FOREIGN PATENT DOCUMENTS 2194503     1/1996    (CA) .
2 327 412   12/1973   (DE) .
2 357 370    5/1975   (DE) .
24 55 238    5/1975   (DE) .
24 55 887    5/1975   (DE) .
195 02700    8/1995   (DE) .
44 23 612    1/1996   (DE) .
085 890      8/1983   (EP) .
147 879      7/1985   (EP) .
9117138  *  11/1991   (WO) .

OTHER PUBLICATIONS

"Prepn.&Prop.of N–methyl–. . . substituted hydrox.", Choudhary etal.,J.Ch.Eng.Data,30/2,237–9, Feb. 1985.*
"Res.in the azole series", Bouchet,Ph. et al.,Bull.Soc. Chim.Fr.5/6,839–44(1976), May 1976.*
Chem.Abst. XP–002087897, vol. 115, 10/91, No. 17.
Kosak et al., XP 000569987, Hydrogenation of Nitroarenes. . . , 135–147.
Houben–Weyl, Bol. E16a, 1990, 49–52 + translation.

* cited by examiner

Primary Examiner—Richard L. Raymond
Assistant Examiner—Sudhaker B. Patel
(74) Attorney, Agent, or Firm—Keil & Weinkauf

(57) ABSTRACT

The invention relates to a method for producing N-acylated (hetero)aromatic hydroxylamine derivatives of formula (I), wherein the substituents, the ring atom and the index have the meanings give in the Description, by hydrogenating a (hetero)aromatic nitro-compound of general formula (II) in the presence of a hydrogenation catalyst.

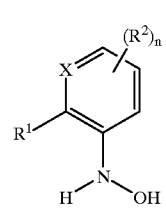

(I)

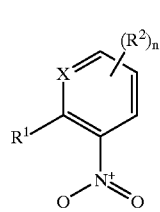

(II)

18 Claims, No Drawings

METHOD FOR PRODUCING (HETERO) AROMATIC HYDROXYLAMINES

The present invention relates to a process for the preparation of (hetero)aromatic hydroxylamine derivates of the formula I

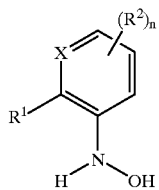

where:

R$^1$ is hydrogen, halogen, cyano, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-alkylcarbonyl, C$_1$–C$_4$-dialkylaminocarbonyl, C$_1$–C$_4$-alkylcarbonylamino, C$_1$–C$_4$-alkylcarbonyl-C$_1$–C$_6$-alkylamino, C$_1$–C$_4$-alkoxycarbonyl, —CH$_2$O —N=C(R$^a$)—C(R$^b$)=N—O—R$^c$, —CH$_2$—O—N=C(R$^d$)—C$_1$–C$_4$-alkyl, or a group A-B, where A is —O—, —CH$_2$—, —O—CH$_2$—, —CH$_2$—O—, —CH$_2$—O—CO—, —CH=CH—, —CH=N—O—, —CH$_2$—O—N=C(R$^a$)- or a single bond, B is phenyl, naphthyl, pyridyl, pyrazinyl, pyrimidinyl, pyridazinyl, pyrazolyl, imidazolyl, oxazolyl, isoxazolyl, thiazolyl, isothiazolyl, 1,2,4-triazolyl, 1,2,3-triazolyl, furanyl, thienyl, pyrrolyl or C$_3$–C$_7$-cycloalkyl, where B may be substituted by 1–3 substituents R$^i$, R$^i$ is hydrogen, halogen, cyano, C–C$_4$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$ -alkylcarbonyl, C$_1$–C$_4$-alkyl-C(R$^d$)=N—O—C$_1$–C$_4$-alkyl, C$_1$–C$_4$-alkoxycarbonyl, C$_1$–C$_4$-alkylaminocarbonyl, C$_1$–C$_4$-dialkylaminocarbonyl, C$_1$–C$_4$-alkylcarbonylamino, C$_1$–C$_4$-alkylcarbonyl-C$_1$–C$_4$-alkylamino or phenyl which itself may be substituted by halogen or C$_1$–C$_4$-alkyl, R$^a$ and R$^c$ are each hydrogen, halogen, cyano, C$_1$–C$_4$-alkyl, C$_1$–C$_4$-alkoxy, C$_1$–C$_4$-alkylthio, cyclopropyl or trifluoromethyl, R$^b$ is C$_1$–C$_4$-alkyl, C$_2$–C$_4$-alkenyl, C$_3$–C$_6$-cycloalkyl, phenyl, hetaryl or heterocyclyl, R$^d$ independently of one another, are hydrogen, C$_1$–C$_4$-alkyl, C$_2$–C$_4$-alkenyl, or C$_2$–C$_4$-alkynyl, R$^2$ is halogen, C$_1$–C$_4$-alkyl, C$_1$–C$_4$-haloalkyl or C$_1$–C$_4$-alkoxycarbonyl, x is N or CH and n is 0, 1, 2 or 3, it being possible for the radicals R$^4$ to be different when n is greater than 1, by hydrogenating a (hetero)aromatic nitro compound of the formula II

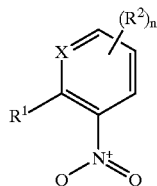

where R$^1$, X and R$^2$ have the abovementioned meanings, in the presence of a hydrogenation catalyst.

The literature (DE-A 2,455,238 and DE-A 2,455,887) describes the preparation of phenylhydroxylamines by catalytic reduction of nitroaromatics in the presence of aromatic amines such as pyridine. DE-A 2,357,370 and DE-A 2,327,412 describe a similar process with the aid of heterocyclic amines, such as piperidine. In all these publications, the amine simultaneously acts as a solvent. The yields achievable by these processes are, after appropriate working up and purification, 50–85%; if the reaction is carried out in the presence of pyridine, the yield is slightly higher in individual cases. However, carrying out the reaction in pyridine is not very desirable owing to the more complicated working up (higher boiling point, similar solvent properties to the hydroxylamine) and for cost reasons.

A more suitable process for the preparation of (hetero)aromatic hydroxylamines of the formula I of the present invention is described in DE-A 19,502,700. Here, the reaction is carried out in the presence of special heterocyclic amines, ie. N-alkylmorpholines, which, as in the abovementioned publications, also act as the solvent. Although this process leads to higher product yields, it requires large amounts of alkylmorpholines for complete dissolution of the starting material and, owing to adduct formation of the product with the alkylmorpholine used, complicated working up operations for isolating the product. Since the alkylmorpholines cause considerable problems when carrying out the subsequent stages, their concentration must be greatly reduced by means of distillation and they must be completely removed in an additional extraction step. The high thermal load adversely affects the purity and yield of the hydroxylamines, many of which are unstable.

The recycled hydrogenation catalyst loses activity after a few cycles. The costs associated with the regeneration of the catalyst reduce the cost-efficiency of the process.

Finally, GB-A 1,092,027 discloses a hydrogenation process for the preparation of cyclohexylhydroxylamines in the presence of amines. In addition to the abovementioned heterocyclic amines, cyclohexylamine, an alicyclic amine, is preferably used in this process. The addition of a protic solvent, such as ethanol, leads to a substantially lower yield in the examples described. With respect to the reaction temperature, the amine used and any solvent added, the different type of substrate requires specific conditions (90° C., cyclohexylamine, ethanol), which cannot be applied to hydrogenation of (hetero)aromatic nitro compounds.

It is an object of the present invention to provide a process for the preparation of E-acylated (hetero)aromatic hydroxylamines which does not have the disadvantages described.

We have found that this object is achieved by the process mentioned at the outset, wherein the hydrogenation is carried out in a mixture of an inert, aprotic solvent and an aliphatic amine.

The surprising aspect of this process is that particularly aliphatic amines give good hydrogenation results although the prior art explicitly indicates the use of (hetero)aromatic and heterocyclic amines. Furthermore, when aliphatic amines are used, there is a lower level of adduct formation with the hydroxylamine. A major part of the amine can thus be removed in a gentle manner by distillation or extraction.

Also surprising is that the hydrogenation in the presence of aliphatic amines can be improved by adding a nonpolar, aprotic solvent, in such a way that the formation of undesirable byproducts, such as azoxy compounds, is substantially absent and hence the crude hydrogenation mixture obtained after removing the amine can be used directly in the subsequent stages.

Finally, it was not expected that the hydrogenation catalyst would have substantially longer time-on-stream in the novel process than in the process described and using N-alkylmorpholines.

The novel process is preferably suitable for the preparation of (hetero)aromatic compounds of the formula I, where
$R^1$ is —$CH_2$—O—N=($R^a$)—C($R^b$)=N—O—$R^6$, $C_1$–$C_4$-alkyl-$CR^d$=N—O—$C_1$–$C_4$-alkyl or a group A-B where A, B, $R^a$, $R^b$, $R^c$ and $R^d$ and $R^2$, X and n have the meanings stated in claim 1.

In particular, the novel process can be used to prepare the intermediates, stated in WO 96/01256, for III$a$ and crop protection agents IV$a$.

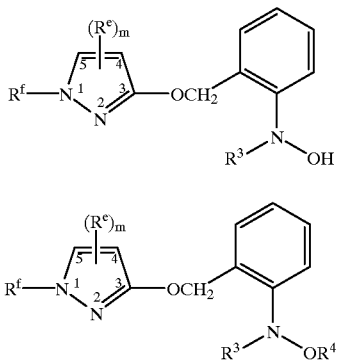

in which
$R^f$ is $C_1$–$C_6$-alkyl, $C_2$–$C_6$-alkenyl, $C_2$–$C_6$-alkynyl, unsubstituted or substituted, saturated or mono- or diunsaturated heterocyclyl or unsubstituted or substituted aryl or hetaryl, $R^e$ is halogen, cyano, $C_1$–$C_4$-alkyl, $C_1$–$C_4$-haloalkyl, $C_1$–$C_4$-alkoxy, $C_1$–$C_4$-alkylthio or $C_1$–$C_4$-alkoxycarbonyl and m is 0, 1, 2, and $R^3$ and $R^4$ have the meanings stated in claim 1 (cf. Tables A and B).

TABLE A

IIIa

| No. | $R^e$ | m | $R^f$ | $R^3$ | mp. [° C.], IR [cm$^{-1}$] |
|---|---|---|---|---|---|
| IIIa.1 | — | 0 | $C_6H_5$ | $COOCH_3$ | 1718, 1600, 1545, 1507, 1481, 1458, 1399, 1359, 1032, 757 |
| IIIa.2 | — | 0 | $C_6H_5$ | $CONHCH_3$ | 1653, 1601, 1545, 1707, 1479, 1454, 1414, 1398, 1355, 755 |
| IIIa.3 | — | 0 | $C_6H_5$ | $COCH_3$ | 1643, 1622, 1601, 1544, 1493, 1480, 1368, 1027, 759, 745 |
| IIIa.4 | — | 0 | $C_6H_5$ | $COC_2H_5$ | 1619, 1600, 1550, 1495, 1482, 1462, 1454, 1358, 765, 753 |
| IIIa.5 | — | 0 | 4-Cl—$C_6H_4$ | $COOCH_3$ | 105 |
| IIIa.6 | — | 0 | 4-Cl—$C_6H_4$ | $CONHCH_3$ | 1653, 1546, 1503, 1480, 1455, 1426, 1390, 1357, 1094, 1071 |

TABLE B

IVa

| No. | $R^e$ | m | $R^f$ | $R^4$ | $R^3$ | mp. [° C.], IR [cm$^{-1}$] |
|---|---|---|---|---|---|---|
| IVa.1 | 5-$CH_3$ | 1 | 4-Cl—$C_6H_4$ | $CH_3$ | $COOCH_3$ | 1738, 1561, 1500, 1456, 1440, 1359, 1094, 1010, 764 |
| IVa.2 | 4-$CF_3$ | 1 | cyclohexyl | $CH_3$ | $COOCH_3$ | 1743, 1496, 1456, 1441, 1359, 1272, 1262, 1176, 1124, 1029 |
| IVa.3 | 4-Cl | 1 | 5-Cl-pyridin-2-yl | $CH_3$ | $COOCH_3$ | 92 |
| IVa.4 | 4-$H_3CO_2C$ | 1 | $CH_2C_6H_5$ | $CH_3$ | $COOCH_3$ | 71 |
| IVa.5 | — | 0 | $C_6H_5$ | $CH_3$ | $CONHCH_3$ | 1675, 1600, 1545, 1508, 1479, 1462, 1399, 1355, 1054, 756 |
| IVa.6 | — | 0 | $C_6H_5$ | $CH_3$ | $COCH_3$ | 1680, 1600, 1545, 1507, 1480, 1456, 1359, 1056, 1032, 758 |

TABLE B-continued

IVa

![IVa structure]

| No. | R$^e$ | m | R$^f$ | R$^4$ | R$^3$ | mp. [° C.], IR [cm$^{-1}$] |
|---|---|---|---|---|---|---|
| IVa.7 | — | 0 | C$_6$H$_5$ | CH$_3$ | COC$_2$H$_5$ | 1678, 1600, 1545, 1480, 1456, 1394, 1378, 1358, 1055, 756 |
| IVa.8 | — | 0 | 2,4-Cl$_2$-phenyl | CH$_3$ | CONHCH$_3$ | 130 |

The compounds III and IV are preferably prepared by N-acylation of the hydroxylamines I prepared by the novel process to give the compounds III and subsequent O-alkylation to give the compounds IV (cf. Scheme 1).

Scheme 1

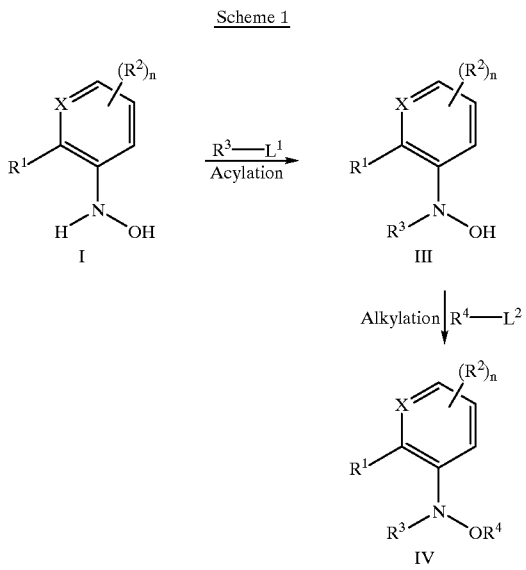

The acylation and alkylation are described after the hydrogenation.

Primary, secondary or tertiary aliphatic amines are employed in the novel process. Aliphatic amines are understood to be those amines having one or more straight-chain or branched C$_1$–C$_6$-alkyl radicals. Preference is given to those aliphatic amines whose boiling point is preferably below that of the inert, aprotic solvent used. Owing to the lower boiling point, the amines can be removed by distillation in a gentle manner. Furthermore, the stated boiling point requirement means that the amines have a small alkyl chain length and hence, as a rule, also have good water solubility, which in turn permits simple extraction of the amines by means of water.

In a preferred embodiment of the process, primary C$_1$–C$_4$-alkylamines are used. n-Propyl-, isopropyl-, n-butyl- and tert-butylamine are preferred, n-propylamine being particularly preferred. The C$_1$–C$_4$-alkylamines all have a low boiling point and good water solubility. Moreover, it is found that, in the further conversion of the hydroxylamines I into N-acylated compounds III or O-alkylated compounds IV, residual amounts of these amines are not troublesome, whereas even small amounts of, for example, n-alkylmorpholines lead to lower yields in these subsequent reactions. The use of the C$_1$–C$_4$-alkylamines thus permits a further simplification of the working up of the hydrogenation mixture and makes a decisive contribution to the process capability of a process for the preparation of compounds III and IV.

For example aliphatic or cyclic ethers such as tetrahydrofuran or preferably aliphatic or aromatic hydrocarbons such as benzene, toluene or chlorobenzene are used as inert, aprotic solvents.

As a rule, the amine is used in a concentration of from 0.1 to 20, preferably from 0.1 to 15, % by weight in the solvent. Higher concentrations are possible but usually result in scarcely any improvements in the yield and selectivity and are therefore uneconomical.

The chosen temperature range for the novel hydrogenation is from –20° C. to +30° C., preferably from –5 to +10° C. The minimum temperature is determined only by the freezing point of the solvent used. The maximum temperature is dependent on the nitro compound to be hydrogenated and on the reaction parameters. To avoid overhydrogenation, a pressure which is from atmospheric pressure to 10 bar gauge pressure is established at the temperature at which the hydrogenation takes place sufficiently rapidly. Usually, the hydrogen gas is introduced into the hydrogenation reactor at atmospheric or slightly superatmospheric pressure.

The starting materials need not be present in dissolved form for carrying out the novel process. The reaction gives optimum results even in suspension.

The amine is used, as a rule, in a molar ratio of from 1 to 15, based on the nitro compound II.

In the novel process, commercial catalysts which contain, for example, platinum or palladium on a carrier, or Raney nickel or Raney cobalt, are used. If starting materials which contain sensitive groups, for example halogens or benzyl ethers, are to be hydrogenated in the process with the use of platinum or palladium catalysts, the catalyst may have to be doped with sulfur or selenium in order to obtain sufficient selectivity. After a reaction cycle, the catalyst can be filtered off and reused without noticeable loss of activity.

The use of a platinum or palladium catalyst is preferred. The platinum or palladium content of the catalyst is not critical and may be varied within wide limits. A content of from 0.1 to 15, preferably from 0.5 to 10, % by weight, based on the carrier material, is advantageous. The amount of platinum or palladium used is from 0.001 to 1, preferably from 0.01 to 0.1, % by weight, based on the nitro compound.

In the batchwise hydrogenation, the catalyst is preferably used in the form of a powder. In a preferred embodiment, operation is continuous and the catalyst used on the carrier material carbon is platinum or palladium. Other nonamphoteric carriers, such as graphite, $BaSO_4$ or SiC, are also possible.

After the end of the reaction, a major part of the added amine is distilled off or is extracted with water. The distillation is preferably carried out under nitrogen or at reduced pressure. In the case of sensitive hydroxylamines, it is essential to ensure the complete absence of oxygen.

Since the handling of the generally oxygen-sensitive hydroxylamines is difficult in some cases, it may be advantageous to process the bydroxylamines I further immediately after removal of the aliphatic amine by extraction or distillation. In the removal of the amine by distillation, it is advantageous if the amine has a lower boiling point than the solvent. A solution of the hydroxylamine in the solvent is obtained and can be further processed immediately.

For the preparation of the R-acylated compounds III and O-alkylated compounds IV, the hydroxylamines I, preferably directly after removal of the aliphatic amine by distillation or extraction, without further purification, are N-acylated to give the compounds of the formula III

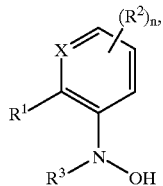

III where $R^1$ and $R^2$, the ring atom X and n have the meanings stated in claim 2 and $R^3$ is $C_1$–$C_4$-alkoxycarbonyl, $C_1$–$C_4$-alkylcarbonyl, $C_1$–$C_4$-alkylaminocarbonyl or di($C_1$–$C_4$-alkyl)aminocarbonyl, with the aid of an acylating agent $R^3$-$L^1$, where $L^1$ is a nucleophilic leaving group, such as halide, hydroxide, anhydride or isocyanate, and then, if required, O-alkylated to give the compounds of the formula IV

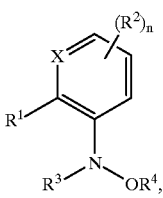

IV where $R^1$, $R^2$ and $R^3$, the ring atom X and n have the abovementioned meanings and $R^4$ is $C_1$–$C_6$-alkyl, with the aid of an alkylating agent $R^4$-$L^2$, where $L^2$ is a nucleophilic leaving group, such as halide, sulfate or sulfonate.

The reaction of the hydroxylamines I with acylating agents $R^3$-$L^1$, where $R^3$ has the meanings stated above and $L^1$ is a nucleophilic leaving group, eg. chloride, is generally carried out under alkaline conditions.

Examples of suitable acylating agents are acid chlorides, $C_1$–$C_4$-alkyl chloroformates, such as methyl chloroformate, $C_1$–$C_4$-alkanecarbonyl chlorides, $C_1$–$C_4$-alkylcarbamoyl chlorides, di-$C_1$–$C_4$-alkylcarbamoyl chlorides, anhydrides and isocyanates.

As acylating agents the free acids in combination with a condensation agent, eg. carbonyldiamidazole or dicyclohexylcarbodiimide, or the corresponding anhydrides may be used.

The acylation is advantageously carried out in the presence of an inert organic solvent which was used in the hydrogenation in [sic], for example in an aprotic solvent, such as an aliphatic or aromatic hydrocarbon, eg. toluene, xylene, heptane or cyclohexane, or in an aliphatic or cyclic ether, preferably 1,2-dimethoxyethane, tetrahydrofuran or dioxane. It is also possible to add a polar aprotic solvent, such as an aliphatic ketone, preferably acetone, an amide, preferably dimethylformamide, or a sulfoxide, preferably dimethyl sulfoxide, ureas, eg. tetramethylurea or 1,3-dimethyltetrahydro-2(1 H)-pyrimidinone, a carboxylic ester, such as ethyl acetate, or a halogenated aliphatic or aromatic hydrocarbon, such as dichloromethane or chlorobenzene, to the reaction mixture.

As a rule, the reaction is carried out in the presence of an inorganic base, such as sodium hydroxide, potassium hydroxide, sodium carbonate, sodium bicarbonate, potassium carbonate or potassium bicarbonate, an amine, such as triethylamine, pyridine or N,N-diethylaniline, or an alkali metal alcoholate, eg. sodium methylate or ethylate or potassium tert-butylate. However, the base is not absolutely essential and can, if required, be replaced by other acid acceptors, for example basic ion exchangers or water.

The reaction temperature of the acylation is in general from 0° C. to the reflux temperature of the solvent used, preferably from 0 to 50° C.

The reaction can also be carried out in a two-phase system consisting of a solution of alkali metal or alkaline earth metal hydroxides or carbonates in water and an organic phase. Suitable phase-transfer catalysts here are, for example, ammonium halides and tetrafluoroborates and phosphonium halides. Tetrabutyl-ammonium chloride and benzyltriethylammonium chloride are particularly preferred.

The alkylation is usually carried out in an inert solvent or diluent, preferably in the presence of a base.

Examples of suitable solvents or diluents are those mentioned in the acylation described above.

Usually, a halide, preferably a chloride or bromide, a sulfate, preferably dimethyl sulfate, a sulfonate, preferably a methanesulfonate (mesylate), benzenesulfonate, o-toluenesulfonate (tosylate) or p-bromobenzenesulfonate (brosylate) or trifluoromethanesulfonate (triflate), or a diazo compound of an alkane is used for the alkylation.

Suitable bases are inorganic bases, for example carbonates, such as potassium carbonate or sodium carbonate, bicarbonates, such as potassium bicarbonate or sodium bicarbonate, hydroxides, such as sodium hydroxide or potassium hydroxide, alkali metal hydrides, for example sodium hydride or potassium hydride, organic bases, such as amines, eg. triethylamine, pyridine or N,N-diethyl-aniline, and alkali metal alcoholates, such as sodium methylate or ethylate or potassium tert-butylate.

Preferably, the alkylating agent (for example dimethyl sulfate) and the N-acylated hydroxylamine III are initially taken and the base (for example potassium hydroxide) is metered in.

The amount of base or alkylating agent is preferably from half the molar amount to twice the molar amount, based on the amount of the compound III. Base and alkylating agent are particularly preferably used in a slight excess.

In general, the reaction temperature in the alkylation is from –78° C. to the boiling point of the reaction mixture, preferably from 0 to 100° C. and particularly preferably from 60 to 90° C.

As in the case of the acylation, the alkylation, too, can be carried out in a two-phase system. The abovementioned phase-transfer catalysts may be used.

The novel process is presented below by means of examples.

EXAMPLE 1

N-Hydroxy-N-2-[N'-(p-chlorophenyl)pyrazol-3'-yloxymethyl]aniline a) Hydrogenation with n-propylamine in toluene with catalyst Pt/C 60 g (182 mmol) of 2-[N-(p-chlorophenyl)pyrazol-3'-yloxymethyl]-nitrobenzene in 700 ml of toluene were introduced, with stirring, into a 750 ml flask having a gas inlet tube. After cooling to about 5° C., 72.8 g (14% by weight, based on toluene) of n-propylamine and 33 g of platinum on carbon (2.5%) were added and the reaction vessel was flushed with hydrogen at 5° C. The hydrogenation was carried out at a constant hydrogen pressure of 100 bar. According to HPLC analysis, the reaction was complete after 2 hours. The reaction vessel was flushed with nitrogen, after which the n-propylamine was distilled off at 100–150 mbar and 40–50° C.

430 ml of a solution in toluene were obtained which, according to HPLC analysis, contained 54.8 g of N-hydroxy-N-2-[N'-(p-chlorophenyl)pyrazol-3'-yloxymethyl]-aniline (93.4% yield).

b) Hydrogenation with n-propylamine in toluene with catalyst Pt/SiC

The hydrogenation was repeated using 1% of Pt on SiC as catalyst under conditions otherwise described in Example 1a. After removal of the catalyst, the hydroxylamine described in Example 1a was obtained in a yield of 94.2%.

c) Hydrogenation with n-butylamine in chlorobenzene 42 g (0.57 mol) of n-butylamine and 1.9 g of 5% Pt/C (F 105 XRS/W from Degussa) were added to a solution of 19 g (57 mmol) of 2-[N-(p-chlorophenyl)pyrazol-3'-yloxymethyl]-nitrobenzene in 500 ml of chlorobenzene. After cooling to about 5° C. and flushing with nitrogen and hydrogen, hydrogenation was carried out at from 5 to 7° C. at a constant hydrogen pressure of 100 mbar. According to HPLC analysis, the reaction was complete after 35 minutes. After the reaction vessel had been flushed with nitrogen, the catalyst was filtered off and the reaction solution was evaporated down at 40° C. and under reduced pressure of 30–400 mbar. 16.7 g of residue were obtained which, according to HPLC analysis, contained 94.4% by weight of the title compound, corresponding to a yield of 87%.

EXAMPLE 2

Preparation of ethyl N-hydroxy-N-(2-[N'-(p-chlorophenyl)-pyrazol-3'-yloxymethyl]phenyl) carbamate i) N-Hydroxy-N-2-[N,-(p-chlorophenyl)pyrazol-3'-yloxymethyl]-aniline corresponds to Example 1a ii) Methyl N-hydroxy-N-(2-[N'-(p-chlorophenyl)pyrazol-3'-yloxy-methyl]phenyl)carbamate 51 g of toluene and 33 g of water were added, at 30° C. under nitrogen, to the toluene solution obtained from the distillation. 19 g (0.19 mol) of methyl chloroformate were added to the resulting emulsion with thorough stirring in the course of 2 hours. Stirring was carried out for a further 2.5 hours at 30° C., after which the precipitate was filtered off at 15° C. and dried under reduced pressure at 40° C. 59.7 g of the title compound (according to $^1$H-NMR>95% strength by weight) were obtained, corresponding to a yield of 88% over both stages.

EXAMPLE 3 (COMPARATIVE EXAMPLE)

The following comparative experiments for the preparation of N-hydroxy-N-2-[N'-(p-chlorophenyl)pyrazol-3'-yloxymethyl)aniline were carried out:

a) Reaction in primary amine as solvent

After the addition of 1.2 g of 5% Pt/C (F 105 XRS/W 55 from Degussa) and blanketing with nitrogen and flushing with hydrogen at 0° C., the amount of hydrogen theoretically required for complete conversion was passed into a solution of 15 g (45 mmol) of 2-[N-(p-chlorophenyl)pyrazol-3-yloxy-methyl]nitrobenzene in 216 g of n-propylamine at from 0 to 5° C. and 100 bar gauge pressure for 25 minutes. The HPLC analysis of the reaction solution indicated, in addition to traces of the starting material and about 55% by weight of the desired product, also about 22% by weight of the azoxy compound of molar mass 614.

b) Reaction with solvent without amine 15 g (45 mmol) of 2-[N-(p-chlorophenyl)pyrazol-3-yloxy-methyl]nitrobenzene were dissolved in 350 ml of toluene, and 1.2 g of 5% Pt/C (F 105 XRS/W 55 from Degussa) were added. After blanketing and flushing with hydrogen at 0° C., hydrogenation was carried out at from 0 to 5° C. and 100 mbar gauge pressure for 3 h. After this time, about 90% of starting material and about 10% of the desired product were still detected. The experiment was terminated.

c) Reaction with N-methylmorpholine (analogous to DE-A 195 02 700)

10 g of Pt/C catalyst (F 105 XRS/W 55 from Degussa) were added to a solution of 120 g of 2-[N-(p-chlorophenyl)-pyrazol-3'-yloxymethyl) nitrobenzene and 10 g of active carbon in 2.2 l of N-methylmorpholine at about 20° C. After flushing with nitrogen and hydrogen, hydrogenation was carried out at from 20 to 30° C. and a constant hydrogen pressure of 100 mbar for about 2.5 hours. Thereafter, the catalyst was filtered off and the reaction mixture was evaporated down at 50° C. and 20 mbar. To displace the remaining amount of N-methyl-morpholine, about 700 ml of gasoline 186-213 were added and the mixture was again evaporated down at 50–60° C. and 0.5 mbar. The product obtained was dissolved in 85 ml of methanol and the solution was cooled to 0° C. The precipitate obtained was filtered off with suction and dried at 30° C. under reduced pressure. 92.7 g of the desired product (according to HPLC 95% strength by weight) were obtained, corresponding to a yield of 81%.

EXAMPLE 4 (COMPARATIVE EXAMPLE SIMILAR TO DE-A 19,502,700)

Preparation of methyl N-hydroxy-N-(2-[N'-(p-chlorophenyl)-pyrazol-3'-yloxymethyl]phenyl) carbamate i) N-Hydroxy-N-2-[N'-(p-chlorophenyl)pyrazol-3'-yloxymethyl]-aniline corresponds to Example 3c.

ii) Methyl N-hydroxy-N-(2-[N'-(p-chlorophenyl)pyrazol-3'-yl-oxymethyl]phenyl)carbamate The reaction was carried out similarly to Example 2ii) and gave a yield of 93%. The yield achieved over both stages was thus 75%.

EXAMPLE 5

N-(2-Tolyl)hydroxylamine

Hydrogenation in the presence of n-propylamine 41.1 g (0.3 mol) of o-nitrotoluene in 600 ml of toluene were initially taken with 5.1 g of active carbon, with stirring, in a 1.5 l hydrogenation flask having a gas inlet tube. After cooling to about 5–8° C., 67.4 g (1.1 mol) of n-propylamine and 3 g of platinum on carbon (5%) (CF 105 XRS from Degussa) were added and the reaction vessel was flushed at 5° C. with nitrogen and then with hydrogen. The hydrogenation was carried out at a constant hydrogen pressure of 100 mbar gauge pressure. According to HPLC analysis, the reaction was complete after 100 minutes.

The reaction vessel was flushed with nitrogen, after which the amine was distilled off at 60° C. According to HPLC analysis, the N-(2-tolyl)hydroxylamine was present in a purity of 98–99% in solution in toluene.

EXAMPLE 6 (COMPARATIVE EXAMPLE)

N-(2-Tolyl)hydroxylamine

Hydrogenation in the presence of N-methylmorpholine

A suspension of 411 g (3 mol) of 2-nitrotoluene and 15 g of platinum on active carbon (F 105 XRS/W 5% from Degussa) in 2.8 l of 4-methylmorpholine was flushed at 0° C. with nitrogen and then with hydrogen. The reaction was carried out at 100 mbar gauge pressure. The reaction was completed after 13 hours. The mixture was flushed with nitrogen and the catalyst was filtered off, after which the solvent was very substantially distilled off at from 45 to 50° C. under reduced pressure. The residue was taken up in 1 l of 1:1 methylene chloride/water and the aqueous phase was acidified with hydrochloric acid and then extracted with methylene chloride. The organic phases were dried and the solvent was distilled off, after which the residue was digested in pentane and the product was filtered off and washed. 305 g of the title compound were obtained as (according to HPLC analysis) 89% strength by weight product.

EXAMPLE 7

The surprisingly better suitability of the reaction solution with residues of the added amine from the novel process for direct further reaction of the reaction product with methyl chloroformate could be shown by the following comparative experiments:

Methyl N-hydroxy-N-(2-[N'-(p-chlorophenyl)pyrazol-3'-yloxy-methyl]phenyl)carbamate I) According to the invention in the presence of n-propylamine:

1.4 ml of N-propylamine were added to a suspension of 10 g of N-hydroxy-2-[N'-(p-chlorophenyl)pyrazol-3'-yloxymethyl]aniline in 140 ml of toluene. Thereafter, 3.13 g of sodium bicarbonate were added and 3.1 g of methyl chloroformate were introduced in the course of 10 minutes. Stirring was carried out for about 14 hours at about 20° C., after which the solid was filtered off with suction, washed with water and then dried [lacuna] reduced pressure. 10.8 g of the title compound (according to $^1$H-NMR>95% strength by weight) were obtained, corresponding to a yield of 94%.

II) Similar to DE-A 195 02 700 in the presence of N-methylmorpholine:

The experiment was repeated with the addition of 1.4 ml of N-methylmorpholine under conditions otherwise described in Example 7I. After precipitation, washing and drying of the precipitate, 8 g of the title compound (according to $^1$H-NMR >95% strength by weight) were obtained, corresponding to a yield of 69%.

The acylation is surprisingly insensitive to the presence of about 10% by weight of n-propylamine, whereas the addition of corresponding amounts of N-methylmorpholine leads to a substantial reduction in yield.

We claim:

1. A process for the preparation of a (hetero)aromatic hydroxylamine compound of formula I

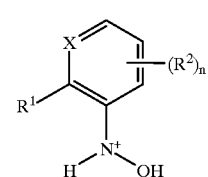

wherein $R^1$ is a group A-B, where

A is —O—, —$CH_2$-, —O—$CH_2$—, —$CH_2$-O—, —$CH_2$-O—CO—, —CH=CH—, —CH=N—O—, —$CH_2$-O—N=C($R^a$)- or a single bond, B is phenyl, naphthyl, pyridyl, pyrazinyl, pyrimidinyl, pyridazinyl, pyrazolyl, imidazolyl, oxazolyl, isoxazolyl, thiazolyl, isothiazolyl, 1,2,4-triazolyl, 1,2,3-triazolyl, furanyl, thienyl, pyrrolyl or $C_3$–$C_7$-cycloalkyl, where B may be substituted by 1–3 substituents $R^i$, $R^i$ is hydrogen, halogen, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylcarbonyl, $C_1$–$C_4$-alkyl-C($R^d$)=N—O—$C_1$–$C_4$-alkylene, $C_1$–$C_4$-alkoxycarbonyl, $C_1$–$C_4$-alkylaminocarbonyl, $C_1$–$C_4$-dialkylaminocarbonyl, $C_1$–$C_4$alkylcarbonylamino, $C_1$–$C_4$-alkylcarbonyl-$C_1$–$C_4$-alkylamino or phenyl which itself may be substituted by halogen or $C_1$–$C_4$-alkyl, $R^a$ is hydrogen, halogen, cyano, $C_1$–$C_4$-alkyl, $C_1$–$C_4$-alkoxy, $C_1$–$C_4$-alkylthio, cyclopropyl or trifluoromethyl, $R^d$ is hydrogen, $C_1$–$C_4$-alkyl, $C_2$–$C_4$-alkenyl, or $C_2$–$C_4$-alkynyl, $R^2$ is halogen, $C_1$–$C_4$-alkyl, $C_1$–$C_4$-haloalkyl or $C_1$–$C_4$-alkoxycarbonyl, X is CH and n is 0, 1, 2 or 3, where the radicals $R^2$ are identical or different when n is greater than 1, which process comprises hydrogenating a (hetero)aromatic nitro compound of formula II

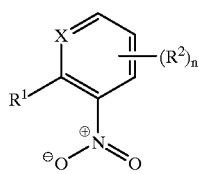

II in the presence of a hydrogenation catalyst, wherein the hydrogenation is carried out in a mixture comprising an inert, aprotic solvent and a $C_1$–$C_4$-alkylamine.

2. The process of claim 1, wherein the $C_1$–$C_4$-alkylamine has a boiling point below that of the solvent.

3. The process of claim 1, wherein the solvent is an aromatic or aliphatic hydrocarbon.

4. The process of claim 1, wherein the hydrogenation catalyst is palladium or platinum, in the presence or absence of an active carbon carrier.

5. The process of claim 1, wherein the hydrogenation catalyst is Raney nickel or Raney cobalt.

6. The process of claim 1, wherein the alykylamine is used in a molar ratio of from 1 to 15, based on the nitro compound II.

7. The process of claim 1, wherein the alkylamine is present in the solvent in a concentration of from 0.1 to 20% by weight.

8. The process of claim 1, further comprising subsequent to the hydrogenation removing the amine by distillation or extraction, and reacting the hydroxylamine I thus obtained, without further purification with an acylating agent $R^3$–$L^1$ wherein $L^1$ is a nucleophilic leaving group, and $R^3$ is $C_1$–$C_4$-alkoxycarbonyl, $C_1$–$C_4$-alkylcarbonyl, $C_1$–$C_4$-alkylaminocarbonyl or di($C_1$–$C_4$-alkyl)aminocarbonyl, to give a compound of formula III

III

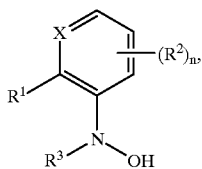

and then optionally reacting the compound of formula III with an alkylating agent $R^4$–$L^2$ wherein $R^4$ is $C_1$–$C_6$-alkyl, and $L^2$ is a nucleophilic leaving group, to give a compound of formula IV

IV

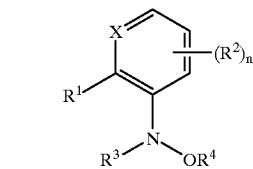

.

9. The process of claim 8, wherein $L^1$ is a halide, a hydroxyl or isocyanate group, or an anhydride residue.

10. The process of claim 8, wherein $L^2$ is a halide, a sulfate or a sulfonate group.

11. The process of claim 1, wherein the alkylamine is a primary amine.

12. The process of claim 11, wherein the alkylamine is n-propylamine, isopropylamine, n-butylamine or tert.-butylamine.

13. The process of claim 11, wherein the $C_1$–$C_4$-alkylamine has a boiling point below that of the solvent.

14. The process of claim 11, wherein the solvent is an aromatic or aliphatic hydrocarbon.

15. The process of claim 11, wherein the hydrogenation catalyst is palladium or platinum, in the presence or absence of an active carbon carrier.

16. The process of claim 11, wherein the hydrogenation catalyst is Raney nickel or Raney cobalt.

17. The process of claim 11, wherein the alkylamine is used in a molar ratio of from 1 to 15, based on the nitro compound II.

18. The process of claim 8, wherein the alkylamine is a primary amine.

* * * * *